United States Patent
Kursun

(10) Patent No.: US 11,269,983 B2
(45) Date of Patent: Mar. 8, 2022

(54) THERMALLY ENRICHED MULTI-MODAL AND MULTI-CHANNEL BIOMETRIC AUTHENTICATION

(71) Applicant: BANK OF AMERICA CORPORATION, Charlotte, NC (US)

(72) Inventor: Eren Kursun, New York City, NY (US)

(73) Assignee: BANK OF AMERICA CORPORATION, Charlotte, NC (US)

( * ) Notice: Subject to any disclaimer, the term of this patent is extended or adjusted under 35 U.S.C. 154(b) by 331 days.

(21) Appl. No.: 16/706,512

(22) Filed: Dec. 6, 2019

(65) Prior Publication Data
US 2021/0173910 A1    Jun. 10, 2021

(51) Int. Cl.
| | |
|---|---|
| *G06F 21/32* | (2013.01) |
| *G06T 7/00* | (2017.01) |
| *G01J 5/48* | (2006.01) |
| *G06K 9/00* | (2006.01) |
| *A61B 5/00* | (2006.01) |
| *H04L 29/06* | (2006.01) |

(52) U.S. Cl.
CPC ............ *G06F 21/32* (2013.01); *A61B 5/7267* (2013.01); *G01J 5/48* (2013.01); *G06K 9/00892* (2013.01); *G06K 9/00906* (2013.01); *G06T 7/0014* (2013.01); *H04L 63/0861* (2013.01); *G06T 2207/10048* (2013.01); *G06T 2207/20084* (2013.01)

(58) Field of Classification Search
CPC ....... G06F 21/32; A61B 5/7267; A61B 5/015; A61B 5/117; G01J 5/48; G06K 9/00892; G06K 9/00906; G06K 9/00979; G06K 9/6271; G06K 9/6289; G06T 7/0014; G06T 2207/10048; G06T 2207/20084; H04L 63/0861
See application file for complete search history.

(56) References Cited

U.S. PATENT DOCUMENTS

| | | | |
|---|---|---|---|
| 6,173,068 B1 * | 1/2001 | Prokoski | G06K 9/00281 382/115 |
| 6,363,485 B1 | 3/2002 | Adams et al. | |
| 6,424,249 B1 | 7/2002 | Houvener | |
| 7,441,123 B2 | 10/2008 | Grant et al. | |
| 7,505,941 B2 | 3/2009 | Bishop et al. | |
| 7,536,557 B2 | 5/2009 | Murakami et al. | |
| 7,616,784 B2 | 11/2009 | Kocher | |

(Continued)

*Primary Examiner* — John B Strege
(74) *Attorney, Agent, or Firm* — Moore & Van Allen PLLC; Nicholas C. Russell

(57) ABSTRACT

Embodiments of the present invention provide an improvement to conventional biometric authentication systems and techniques by providing an innovative system, method and computer program product for thermal enrichment of biometric authentication data to generate a high-confidence verification of user identity. A collaborative system for receiving data and continuously analyzing the data to determine emerging patterns is provided. The invention provides for the enrichment of biometric authentication data with thermal imaging data in order to discern between authentic data samples in contrast to inanimate copies or models. Furthermore, the invention is designed to detect and analyze liveliness of data samples as a means of authentication.

20 Claims, 6 Drawing Sheets

(56) References Cited

U.S. PATENT DOCUMENTS

| | | | |
|---|---|---|---|
| 7,620,265 B1 * | 11/2009 | Wolff | G06T 5/50 |
| | | | 382/254 |
| 7,734,068 B2 | 6/2010 | Fisher | |
| 8,364,972 B1 | 1/2013 | Itoi | |
| 8,899,487 B2 | 12/2014 | Saito et al. | |
| 9,336,634 B2 | 5/2016 | Beenau et al. | |
| 9,852,324 B2 * | 12/2017 | Hough | H04N 5/332 |
| 10,819,923 B1 * | 10/2020 | McCauley | G01S 13/87 |
| 2004/0005086 A1 * | 1/2004 | Wolff | G06K 9/00228 |
| | | | 382/118 |
| 2004/0228507 A1 | 11/2004 | Es | |
| 2009/0037742 A1 | 2/2009 | Narayanaswami | |
| 2009/0037743 A1 | 2/2009 | Narayanaswami | |
| 2009/0100269 A1 | 4/2009 | Naccache | |
| 2009/0116699 A1 | 5/2009 | Turek et al. | |
| 2010/0174914 A1 | 7/2010 | Shafir | |
| 2015/0154436 A1 | 6/2015 | Shi et al. | |
| 2015/0286922 A1 | 10/2015 | Saito et al. | |
| 2017/0169231 A1 | 6/2017 | Chhabra et al. | |
| 2018/0349588 A1 | 12/2018 | Abdelmoneum | |
| 2019/0114098 A1 | 4/2019 | Moran et al. | |

\* cited by examiner

THERMALLY ENRICHED MULTI-MODAL AND MULTI-CHANNEL BIOMETRIC AUTHENTICATION

FIELD OF THE INVENTION

The present invention is generally related to systems and methods for providing an improved authentication system through the use of biometric data and environmental data from multiple channels of input. Multiple devices may be utilized by the multi-channel biometric authentication system in order to receive and process data to authenticate user identities and authorize actions.

BACKGROUND

Existing biometric authentication systems and methods may be susceptible to false authorization in instances where user provide closely modeled data samples that resemble authentic data samples. With the advent of mobile device biometric authentication, the use of biometrics for identity verification has become more prevalent. A need exists for improved systems and methods for detecting authentic data and discerning between imitated data subjects and authentic data features in order to provide high-confidence identity verification.

BRIEF SUMMARY

The following presents a simplified summary of one or more embodiments of the invention in order to provide a basic understanding of such embodiments. This summary is not an extensive overview of all contemplated embodiments and is intended to neither identify key or critical elements of all embodiments, nor delineate the scope of any or all embodiments. Its sole purpose is to present some concepts of one or more embodiments in a simplified form as a prelude to the more detailed description that is presented later.

Embodiments of the present invention address these and/or other needs by providing an innovative system, method and computer program product for the enrichment of biometric authentication data with thermal imaging data in order to discern between authentic data samples in contrast to unauthorized copies or models. A collaborative system for receiving data and continuously analyzing the data to determine emerging patterns and determine unique measurement baselines based on environmental factors is provided. The system is also designed to detect and analyze liveliness of data samples as a means of identity verification. Common characteristics of data may be used to detect patterns that are broadened in scope and used in a generative neural network approach. The thermally enriched biometric authentication system and methods generally comprise: receiving image data and thermal data of an object from one or more devices and channels; combining the received image data and thermal data to produce thermal image data; normalizing the thermal image data based on environmental, device, and channel characteristics; enriching the thermal image data with multimodal biometric data to produce an enriched biometric thermal image; processing the enriched biometric thermal image using a trained neural network model, wherein the processing comprises identification of isothermal curves and normalized thermal gradient coloring on the enriched biometric thermal image; performing an authentication check on the enriched biometric thermal image using the trained neural network model to determine if the isothermal curves and normalized thermal gradient coloring matches known characteristics for a purported identity of the object; and based on the authentication check, verifying or denying the purported identity of the object.

In some embodiments, the invention further comprises performing a liveliness detection on the biometric thermal image, wherein the liveliness detection comprises: analyzing movement, thermal variation, or and distribution of thermal temperature readings across a surface of the object to determine if the object is inanimate or alive; generating an approval if the object is determined to be alive, or generating a denial if the object is determined to be inanimate; and proceeding with the remainder of the system steps only if an approval is generated.

In some embodiments, the multimodal biometric data comprises one or more of hand biometric data, face biometric data, facial feature biometric data, or gait biometric data using both visible and infrared images or video.

In some embodiments, the thermal data is received from multiple channels comprising a mobile device, ATM, entity location device, or third party device.

In some embodiments, the invention further comprises intentionally altering the environmental characteristics surrounding the object; receiving a variety of thermal images of the object; and analyzing the variety of thermal images of the object to produce a dynamic object characteristic pattern.

In some embodiments, the multimodal biometric data further comprises biometric data for multiple features of the object.

In some embodiments, the authentication check fails to determine a match, and the system is further configured to request additional image and thermal data in order to initiate a second attempt at authentication.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
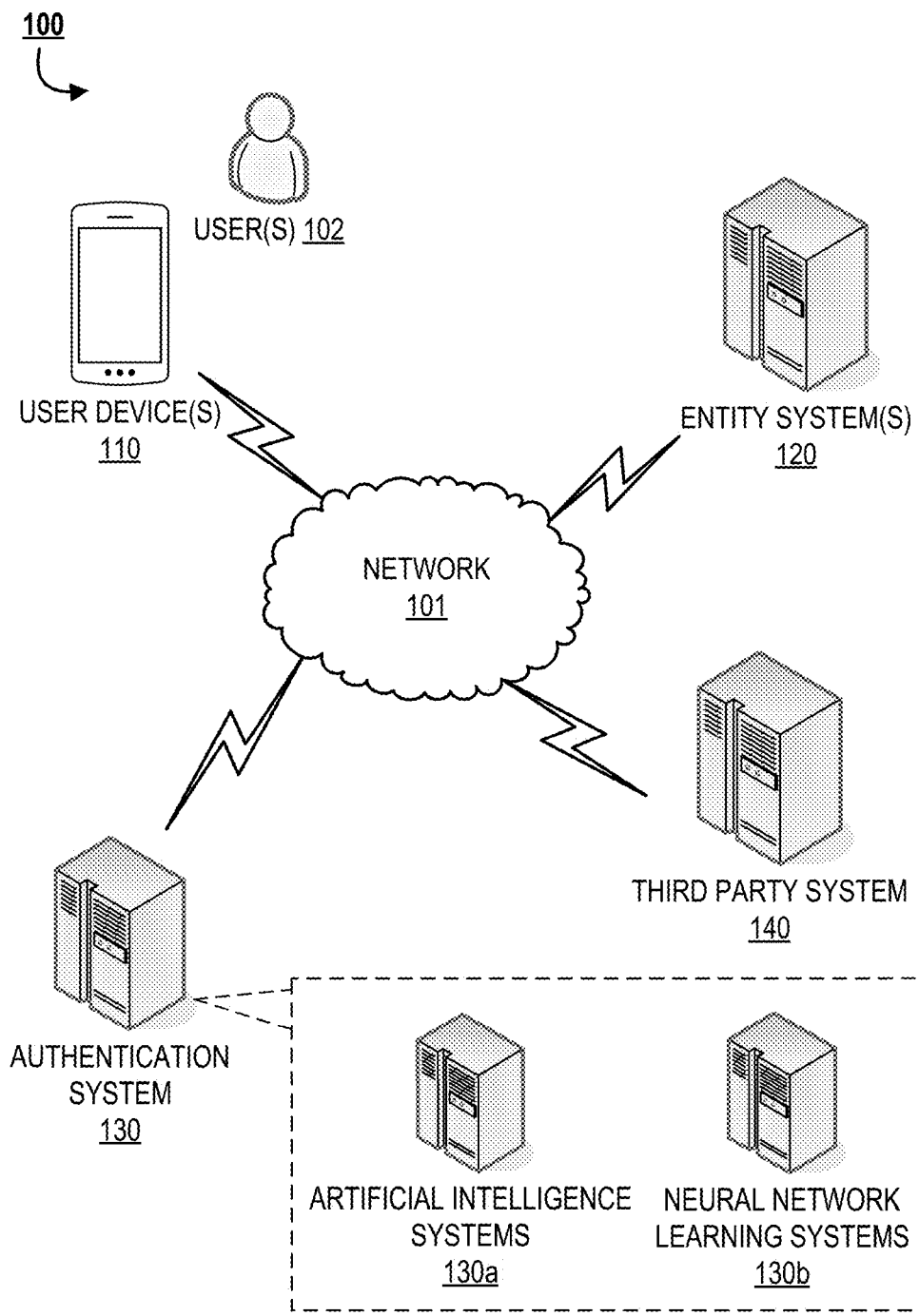
Figure 2:
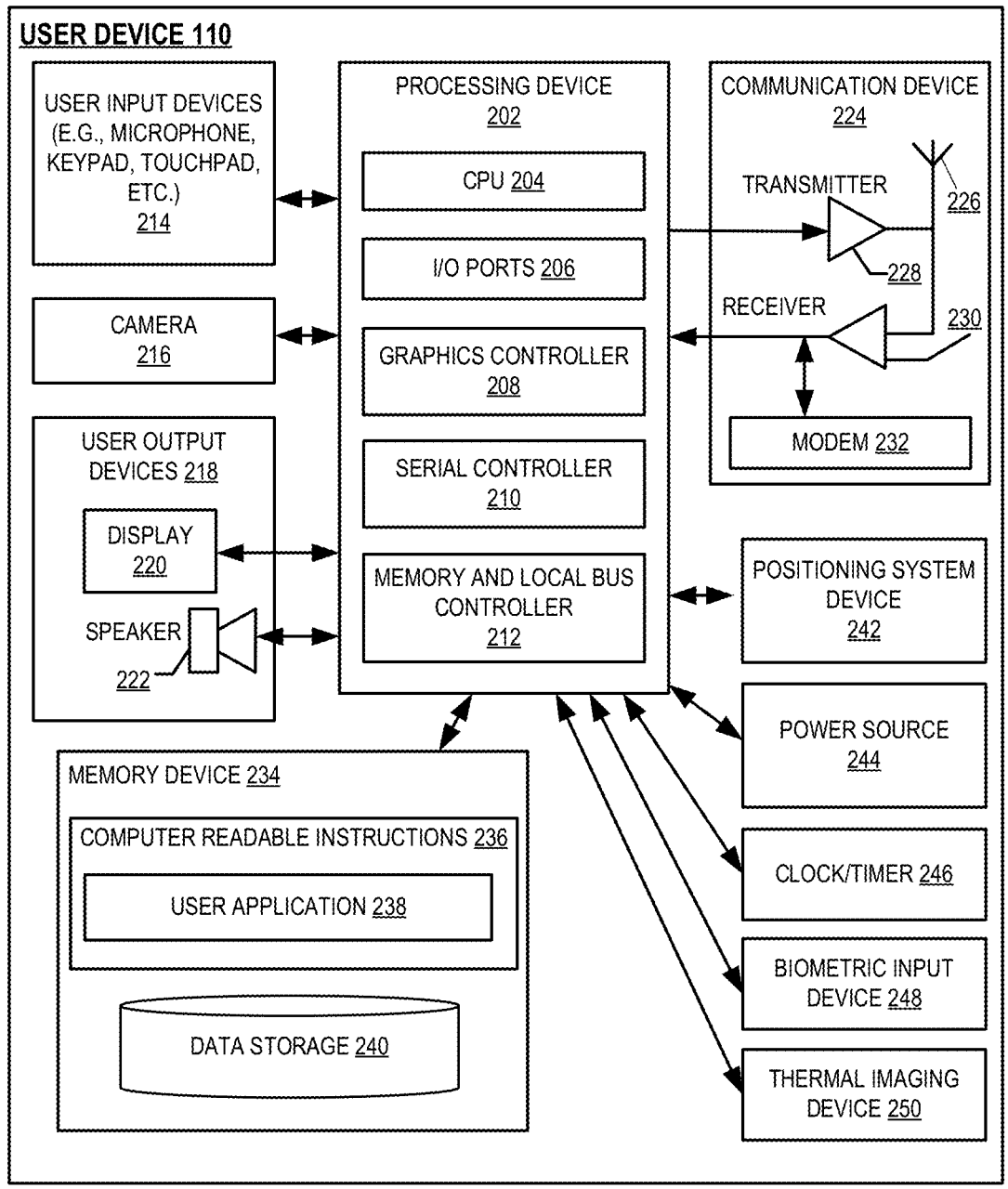
Figure 3:
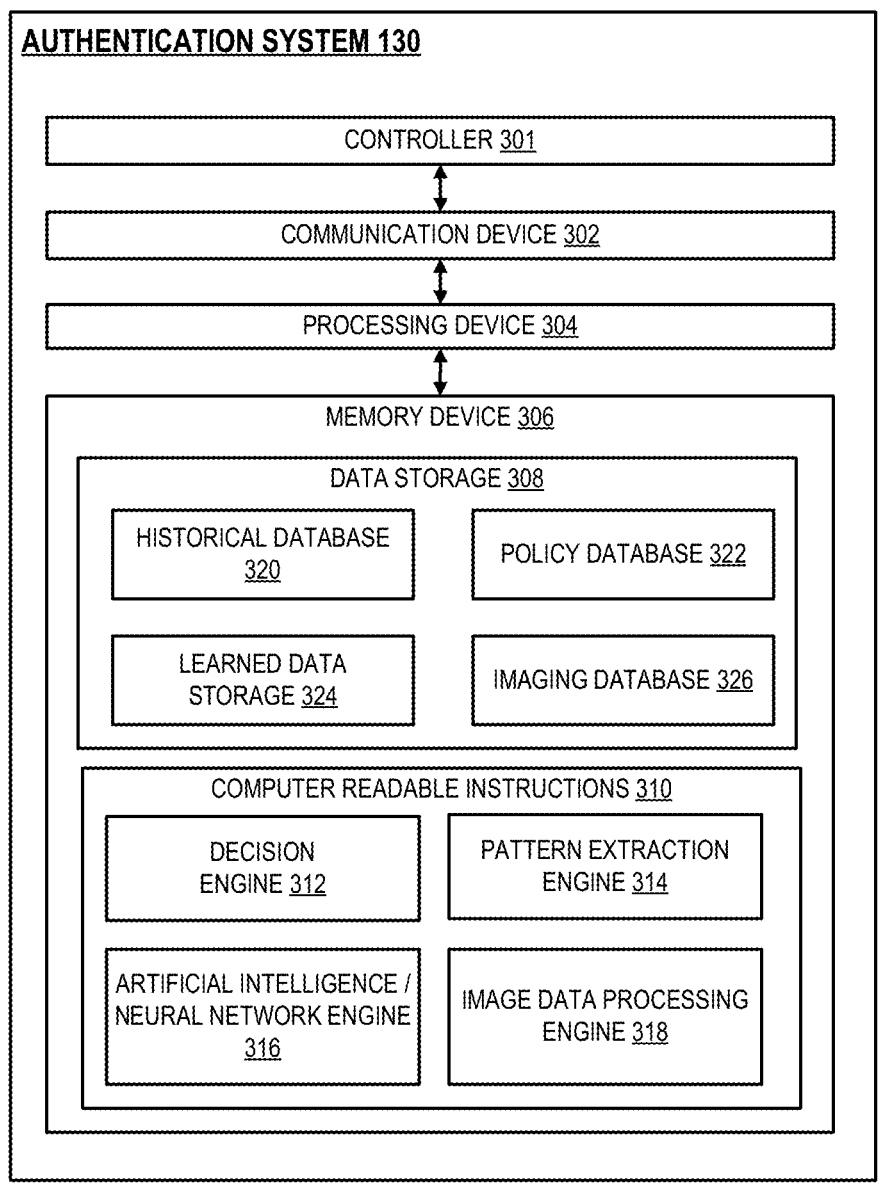
Figure 4:
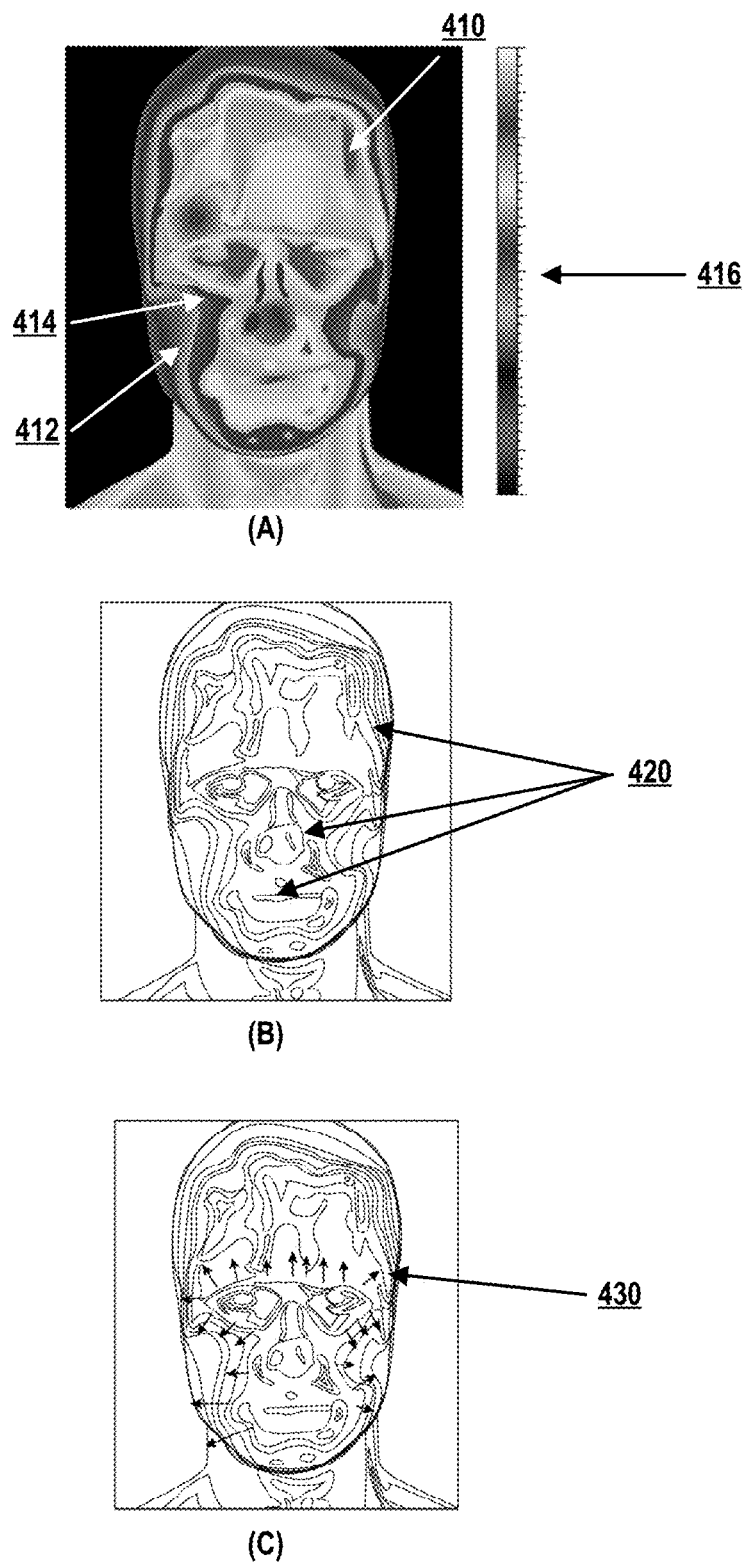
Figure 5:
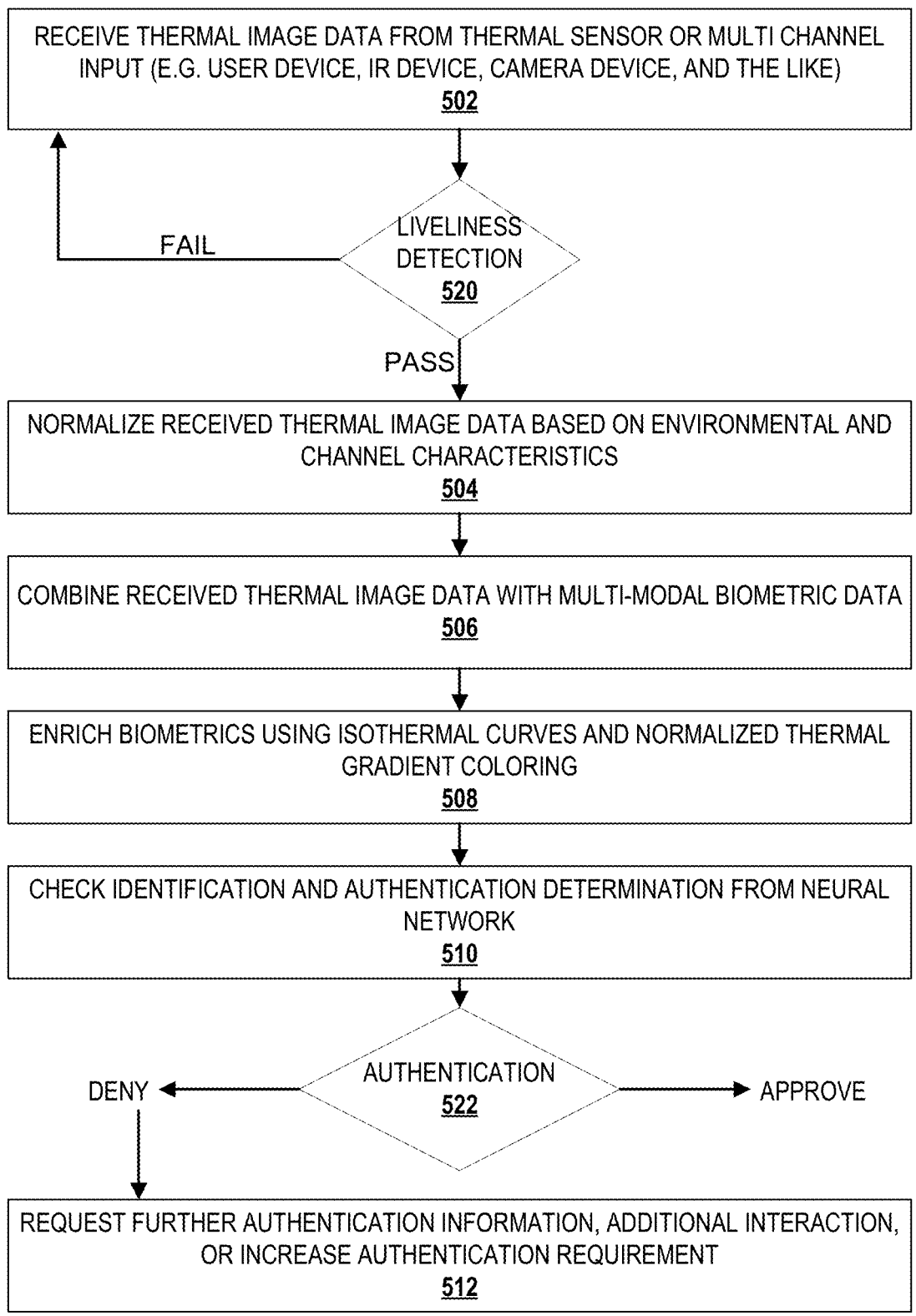
Figure 6:
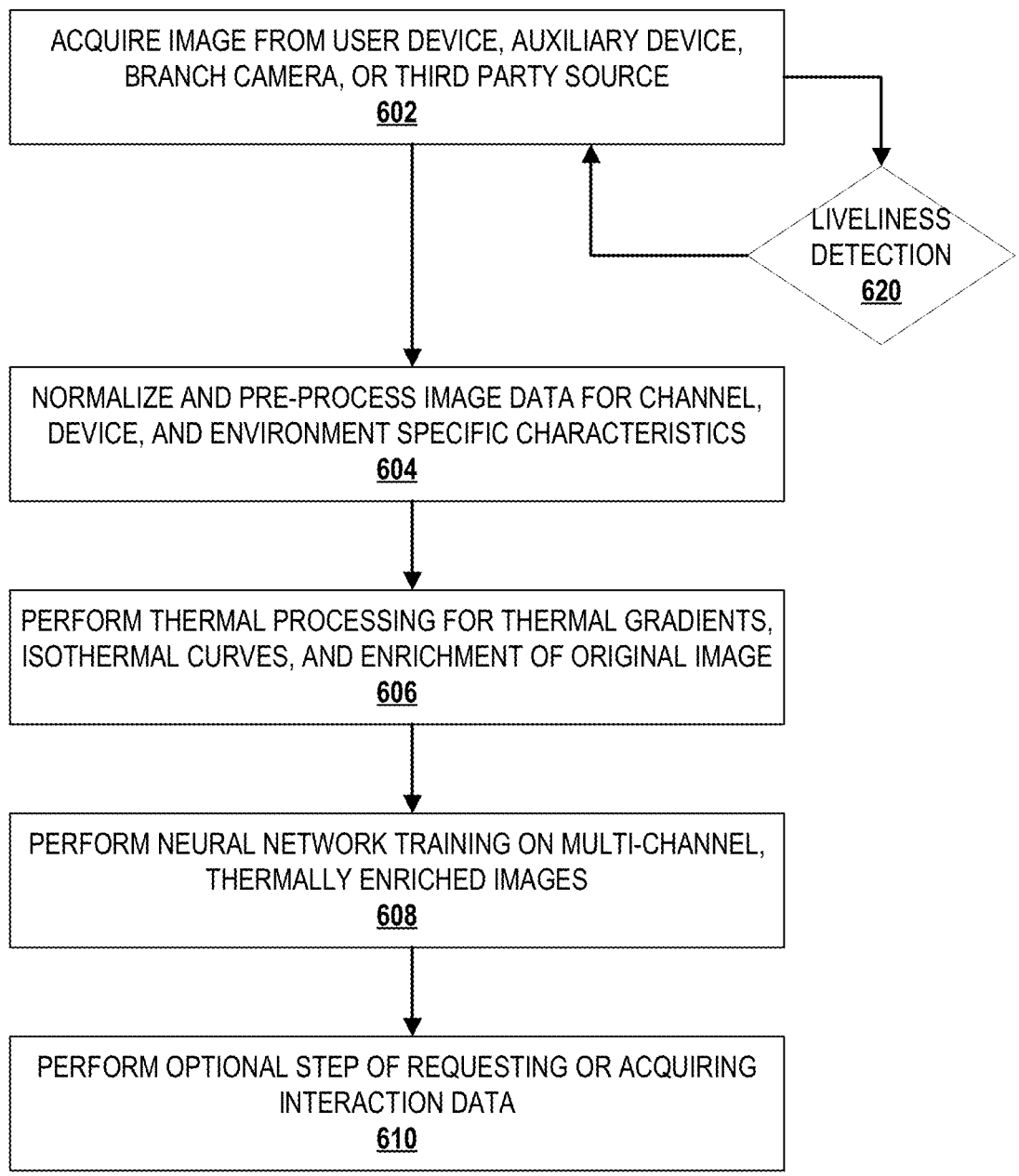

Having thus described embodiments of the invention in general terms, reference will now be made to the accompanying drawings, wherein:

FIG. 1 provides a system environment 100, in accordance with one embodiment of the invention;

FIG. 2 provides a block diagram of a user device 110, in accordance with one embodiment of the invention;

FIG. 3 provides a block diagram of an authentication system 130, in accordance with one embodiment of the invention;

FIG. 4 provides an example of thermal measurement and analysis overlay, in accordance with one embodiment of the invention;

FIG. 5 provides a high level process flow for processing, analysis, and authentication, in accordance with one embodiment of the invention; and FIG. 6 provides a high level process flow for neural network training on multi-modal thermally enriched image data, in accordance with one embodiment of the invention.

DETAILED DESCRIPTION OF EMBODIMENTS OF THE INVENTION

Embodiments of the system, as described herein leverage artificial intelligence, machine-learning, and/or other complex, specific-use computer systems to provide a novel approach for the enrichment of biometric authentication data with thermal imaging data in order to discern between authentic data samples in contrast to unauthorized copies or models. A collaborative system for receiving data and continuously analyzing the data to determine emerging patterns and determine unique measurement baselines based on environmental factors is provided. The system is also designed to detect and analyze liveliness of data samples as a means of identity verification. Common characteristics of data may be used to detect patterns that are broadened in scope and used in a generative neural network approach.

Systems and methods of authentication for high-security applications increasingly rely on the gathering and analysis of biometric data in order to verify user identity. Various implementations exist that employ biometric authentication for a wide array of applications which require a verification of user identity. For instance, secure access to buildings, accounts, devices, user applications, and the like may require biometric authentication in conjunction with or in lieu of conventional passcode based authentication. With the advent of reasonably priced and portable systems and devices which contain high resolution imaging capability, widespread use of biometric authentication has been adopted to provide a secure means of identity verification for a wide range of applications and use-cases. Additionally, the ability for multiple devices to share data over high-speed networks has allowed for remote verification and identity authentication through the use of multiple device systems. In some instances, mobile devices may share data with one or more systems or applications in cases where the user devices have the ability to verify user identity locally and transmit indication of verification to one or more associated systems or third parties.

Biometric authentication mechanisms may, in some instances, use imaging techniques to scan the unique patterns, gradients, and contours in order to create layered 3D maps associated with users' individual physical stature or features. With a high resolution imaging technique, the uniqueness of a user's particular stature or features may provide a low likelihood of a false match under typical circumstances. However, with the development and increased access to technologies such as 3D printing, it may be possible for unauthorized users to create a convincingly similar or identical model of a user's unique stature or physical features that are used for identity verification by one or more systems. As such, a need exists for improved systems and methods for detecting authentic data and discerning between "spoofed" user features in order to provide high-confidence identity verification.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on."

As used herein, the term "user" may refer to any entity or individual associated with the collaborative machine learning system. In some embodiments, a user may be a computing device user, a phone user, a mobile device application user, a customer of an entity or business, a system operator, and/or employee of an entity (e.g., a financial institution). In a specific embodiment, a user may be a managing user of a machine learning model, wherein the system enables the user to reconfigure the model based on user-specified criteria and policies. In another specific embodiment, a user may be a customer accessing a user account via an associated user device, wherein data from an interaction between the user and an entity is analyzed or processed by the system. In some embodiments, identities of an individual may include online handles, usernames, identification numbers (e.g., Internet protocol (IP) addresses), aliases, family names, maiden names, nicknames, or the like. In some embodiments, the user may be an individual or an organization (i.e., a charity, business, company, governing body, or the like).

As used herein the term "user device" may refer to any device that employs a processor and memory and can perform computing functions, such as a personal computer or a mobile device, wherein a mobile device is any mobile communication device, such as a cellular telecommunications device (i.e., a cell phone or mobile phone), a mobile Internet accessing device, or other mobile device. Other types of mobile devices may include laptop computers, tablet computers, wearable devices, cameras, video recorders, audio/video player, radio, global positioning system (GPS) devices, portable digital assistants (PDAs), pagers, mobile televisions, or any combination of the aforementioned. The device may be used by the user to access the system directly or through an application, online portal, internet browser, virtual private network, or other connection channel.

As used herein, the term "entity" may be used to include any organization or collection of users that may interact with the biometric authentication system. An entity may refer to a business, company, or other organization that either maintains or operates the system or requests use and accesses the system. In one embodiment, the entity may be a software development entity or data management entity. In a specific embodiment, the entity may be a cybersecurity entity or misappropriation prevention entity. The terms "financial institution" and "financial entity" may be used to include any organization that processes financial transactions including, but not limited to, banks, credit unions, savings and loan associations, investment companies, stock brokerages, insurance companies and the like. In other embodiments, an entity may be a business, organization, a government organization or the like that is not a financial institution. Particularly with respect to the embodiments depicted in FIGS. 1 through 6, the term entity may refer to the entity which manages or administers the development and use of the authentication system. As used herein, the term "third party" may be an entity, person, or group, other than the entity that manages the authentication system, but may interface with the authentication system by providing data, leveraging the capabilities of the authentication system, and the like.

To "monitor" is to watch, observe, or check something for a special purpose over a period of time. The "monitoring" may occur periodically over the period of time, or the monitoring may occur continuously over the period of time.

In some embodiments, a system may actively monitor a data source, data stream, database, or data archive, wherein the system reaches out to the database and watches, observes, or checks the database for changes, updates, and the like. In other embodiments, a system may passively monitor a database or data stream, wherein the database or data stream provides information to the system and the system then watches, observes, or checks the provided information. In some embodiments, "monitoring" may further comprise analyzing or performing a process on something such as a data source or data stream either passively or in response to an action or change in the data source or data stream. In a specific embodiment, monitoring may comprise continuously monitoring a data stream provided by an imaging device or biometric measurement device in order to analyze changes in the images over time or observe changes in certain objects in different environments.

As used herein, an "interaction" may refer to any action or communication between users, entities, or institutions, and/or one or more devices or systems within the system environment described herein. For example, an interaction may refer to a user interaction with a system or device, wherein the user interacts with the system or device in a particular way. In one embodiment, interactions may be received or extracted from a data stream (e.g., in real-time). An interaction may include user interactions with a user interface (e.g., clicking, swiping, text or data entry, and the like), authentication actions (e.g., signing-in, username and password entry, PIN entry, and the like), biometric authentication actions (e.g., providing a finger print, facial recognition sample, voice sample, and the like), account actions (e.g., account access, fund transfers, and the like) and the like. In another example, an interaction may refer to a user communication via one or more channels (i.e., phone, email, text, instant messaging, brick-and-mortar interaction, and the like) with an entity and/or entity system to complete an operation or perform an action with an account associated with user and/or the entity. A subset of interactions may be referred to herein as "resource actions," which refers to any interaction in which the flow of resources or funds to or from a user resource account may occur. In some embodiments, the authentication system may be used to authenticate a resource action (e.g., authenticate the transfer of funds, access to resource account balances, and the like).

FIG. 1 provides a system environment 100, in accordance with one embodiment of the invention. As illustrated in FIG. 1, authentication system 130 is operatively coupled, via a network 101, to the user device(s) 110 (e.g., a mobile phone, computer, laptop, tablet, terminal, automated teller machine or "ATM", wearable device, and the like), third party system 140, and entity system(s) 120. While only one third party system 140 is depicted in the embodiment shown in FIG. 1, it is understood that the network 101 may interconnect authentication system 130, entity system 120, and user device 110 with multiple third party systems 140. In this way, the authentication system 130 can send information to and receive information from the user device 110, the third party system(s) 140, and the entity system 120. In the illustrated embodiment, the plurality of user devices 110 and systems such as entity system 120 and third party system 140 provide a plurality of communication channels through which the entity system 120, third party system 140, and/or the authentication system 130 may communicate over the network 101. In the illustrated embodiment, the authentication system 130 further comprises an artificial intelligence (AI) system 130a and a machine learning system 130b which may be separate systems operating together with the authentication system 130 or integrated within the authentication system 130.

FIG. 1 illustrates only one example of an embodiment of the system environment 100. It will be appreciated that in other embodiments, one or more of the systems, devices, or servers may be combined into a single system, device, or server, or be made up of multiple systems, devices, or servers. It should be understood that the servers, systems, and devices described herein illustrate one embodiment of the invention. It is further understood that one or more of the servers, systems, and devices can be combined in other embodiments and still function in the same or similar way as the embodiments described herein. Non-limiting examples of applications in which the system described herein may be incorporated include cybersecurity, marketing, misappropriation detection, medicine, autonomous device (e.g., self-driving cars), AI assistants, and the like. In some embodiments, interactions performed between the user device(s) 110 and the third party entity system 120 are intercepted and received by the authentication system 130, wherein interaction data may be extracted from an interaction over the network 101 by the authentication system 130 for analysis. Data monitored and/or extracted by the system may include, in a non-limiting example, user information, communication history, transaction history, and the like. Data, such as user interaction data, may be acquired from across communication channels of an entity such as phone lines, text messaging systems, email, applications (e.g., mobile applications), websites, automated teller machines (ATMs), card readers, call centers, electronic assistants, instant messaging systems, interactive voice response (IVR) systems, brick-and-mortar locations and the like.

The network 101 may be a system specific distributive network receiving and distributing specific network feeds and identifying specific network associated triggers. The network 101 may also be a global area network (GAN), such as the Internet, a wide area network (WAN), a local area network (LAN), or any other type of network or combination of networks. The network 101 may provide for wireline, wireless, or a combination wireline and wireless communication between devices on the network 101.

In some embodiments, the user 102 is an individual interacting with the entity system 120 via a user device 110 while a data flow or data stream between the user device 110 and the entity system 120 is monitored by or received by the authentication system 130 over the network 101 to be processed or analyzed. In some embodiments a user 102 is a user requesting service from the entity (e.g., customer service) or interacting with an account maintained by the entity system 120 in order to initiate or authenticate a resource action. In an alternative embodiment, the user 102 is a user interacting with, maintaining, or employing the authentication system, wherein the system enables the user to reconfigure the model based on user-specified criteria and policies.

FIG. 2 provides a block diagram of the user device 110, in accordance with one embodiment of the invention. The user device 110 may generally include a processing device or processor 202 communicably coupled to devices such as, a memory device 234, user output devices 218 (for example, a user display device 220, or a speaker 222), user input devices 214 (such as a microphone, keypad, touchpad, touch screen, and the like), a communication device or network interface device 224, a power source 244, a clock or other timer 246, a visual capture device such as a camera 216, a positioning system device 242 (e.g., a geo-positioning system device like a GPS device with an included accelerometer, and the like), a biometric input device (e.g., a finger print reader or the like), and a thermal imaging device, such as a specialized imaging device that reads and captures thermal characteristics of the surrounding environment and surrounding objects. The processing device 202 may further include a central processing unit 204, input/output (I/O) port controllers 206, a graphics controller or graphics processing device (GPU) 208, a serial bus controller 210 and a memory and local bus controller 212.

The processing device 202 may include functionality to operate one or more software programs or applications, which may be stored in the memory device 234. For example, the processing device 202 may be capable of operating applications such as the user application 238. The user application 238 may then allow the user device 110 to transmit and receive data and instructions from the other devices and systems of the environment 100. The user device 110 comprises computer-readable instructions 236 and data storage 240 stored in the memory device 234, which in one embodiment includes the computer-readable instructions 236 of a user application 238. In some embodiments, the user application 238 allows a user 102 to access and/or interact with other systems, such as the entity system 120, third party system 140, or authentication system 130. In one embodiment, the user 102 is a maintaining entity of a authentication system 130, wherein the user application enables the user 102 to define policies and reconfigure the authentication system 130. In other embodiments, the user 102 may be a customer of the entity or the third party that is interacting with the authentication system 130 in order to provide authentication data. In one embodiment, the user 102 is a customer of a financial entity and the user application 238 is an online banking application providing access to the entity system 120 wherein the user may interact with a user account via a user interface of the user application 238, wherein the user interactions may be provided in a data stream as an input. In some embodiments, the user 102 may be the subject of the biometric authentication and thermal imaging maps detected by authentication system 130, later to referred to herein as a subset of user called a target user.

The processing device 202 may be configured to use the communication device 224 to communicate with one or more other devices on a network 101 such as, but not limited to the entity system 120 and the authentication system 130. In this regard, the communication device 224 may include an antenna 226 operatively coupled to a transmitter 228 and a receiver 230 (together a "transceiver"), modem 232. The processing device 202 may be configured to provide signals to and receive signals from the transmitter 228 and receiver 230, respectively. The signals may include signaling information in accordance with the air interface standard of the applicable BLE standard, cellular system of the wireless telephone network and the like, that may be part of the network 201. In this regard, the user device 110 may be configured to operate with one or more air interface standards, communication protocols, modulation types, and access types. By way of illustration, the user device 110 may be configured to operate in accordance with any of a number of first, second, third, and/or fourth-generation communication protocols or the like. For example, the user device 110 may be configured to operate in accordance with second-generation (2G) wireless communication protocols IS-136 (time division multiple access (TDMA)), GSM (global system for mobile communication), and/or IS-95 (code division multiple access (CDMA)), or with third-generation (3G) wireless communication protocols, such as Universal Mobile Telecommunications System (UMTS), CDMA2000, wideband CDMA (WCDMA) and/or time division-synchronous CDMA (TD-SCDMA), with fourth-generation (4G) wireless communication protocols, with fifth-generation (5G) wireless communication protocols, and/or the like. The user device 110 may also be configured to operate in accordance with non-cellular communication mechanisms, such as via a wireless local area network (WLAN) or other communication/data networks. The user device 110 may also be configured to operate in accordance with audio frequency, ultrasound frequency, infrared frequency, or other communication/data networks.

The user device 110 may also include a memory buffer, cache memory or temporary memory device operatively coupled to the processing device 202. Typically, one or more applications 238, are loaded into the temporarily memory during use. As used herein, memory may include any computer readable medium configured to store data, code, or other information. The memory device 234 may include volatile memory, such as volatile Random Access Memory (RAM) including a cache area for the temporary storage of data. The memory device 234 may also include non-volatile memory, which can be embedded and/or may be removable. The non-volatile memory may additionally or alternatively include an electrically erasable programmable read-only memory (EEPROM), flash memory or the like.

Though not shown in detail, the system further includes one or more entity systems 120 (as illustrated in FIG. 1) which is connected to the user device 110 and the authentication system 130 and which may be associated with one or more entities, institutions or the like. In this way, while only one entity system 120 is illustrated in FIG. 1, it is understood that multiple networked systems may make up the system environment 100. The entity system 120 generally comprises a communication device, a processing device, and a memory device. The entity system 120 comprises computer-readable instructions stored in the memory device, which in one embodiment includes the computer-readable instructions of an entity application. The entity system 120 may communicate with the user device 110 and the authentication system 130 to provide access to user accounts stored and maintained on the entity system 120. In some embodiments, the entity system 120 may communicate with the authentication system 130 during an interaction with a user 102 in real-time, wherein user interactions may be monitored and processed by the authentication system 130 in order to analyze interactions with the user 102 and reconfigure the neural network model in response to changes in a received or monitored data stream. In one embodiment, the system is configured to receive data for decisioning, wherein the received data is processed and analyzed by the authentication system 130 to determine a decision for verification of a user identity.

FIG. 3 provides a block diagram of the authentication system 130, in accordance with one embodiment of the invention. The authentication system 130 generally comprises a controller 301, a communication device 302, a processing device 304, and a memory device 306.

As used herein, the term "controller" generally refers to a hardware device and/or software program that controls and manages the various systems described herein such as the user device 110, the entity system 120, and/or the authentication system 130, in order to interface and manage data flow between systems while executing commands to control the systems. In some embodiments, the controller may be integrated into one or more of the systems described herein.

In some embodiments, the controller may perform one or more of the processes, actions, or commands described herein.

As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 304 is operatively coupled to the communication device 302 and the memory device 306. The processing device 304 uses the communication device 302 to communicate with the network 101 and other devices on the network 101, such as, but not limited to the user device 110 and the entity system 120. As such, the communication device 302 generally comprises a modem, server, or other device for communicating with other devices on the network 101.

As further illustrated in FIG. 3, the authentication system 130 comprises computer-readable instructions 310 stored in the memory device 306, which in one embodiment includes the computer-readable instructions 310 of a decision engine 312, a pattern extraction engine 314, a pattern extraction engine 314, an artificial intelligence and neural network engine 316, and an image data processing engine 318. In one embodiment, the artificial intelligence and neural network engine 316 may be utilized by the decision engine 312, pattern extraction engine 314, and/or image data processing engine 318 to, respectively, analyze received image data, thermal data, environmental data, and user interaction data in order to identify relevant patterns and user characteristics that can be used to verify user identity authenticate user actions.

In some embodiments, the memory device 306 includes data storage 308 for storing data related to the system environment, but not limited to data created and/or used by the decision engine 312, pattern extraction engine 314, image data processing engine 318, and artificial intelligence and neural network engine 316. Storage of data related to the system environment may include various databases such as historical database 320, policy database 322, learned data storage 324, and imaging database 326.

The historical database 320 is used to store information regarding past interactions (e.g., account actions, transactions, communications, inputs) and/or content of a past data stream. In some embodiments, the historical database 320 may be configured to store data from an incoming data stream of images or thermal data in real-time. In some embodiments, the policy database 322 is configured to store pre-determined policies, conditions, rules, thresholds, user characteristic data, or the like for evaluating and managing the authentication system 130 (e.g., model configurations, user preferences, and model adaptations). The policy database 322 my further be configured to store learned policies, conditions, rules, thresholds, or the like as determined in real-time by the machine learning models of the system described herein. In some embodiments, the policy database 322 is further configured to store metrics, system performance metrics, cost metrics, benefit metrics, cost-change metrics, adversarial scenarios or data, extrapolated scenarios or data, and the like associated with the authentication system 130. In some embodiments, the policy database 322 and/or the historical database 320 include pre-existing training data for training a machine learning or artificial intelligence engine. In some embodiments, the policy database 322 is configured for storing settings associated with the system itself such as energy efficiency settings, computer resource use efficiency settings, response time settings, regulatory guidelines, and the like.

The learned data storage 324 is configured to store data generated by the system (e.g., via decision engine 312, pattern extraction engine 314, artificial intelligence and neural network engine 316, and the like). The data stored in the learned data storage 324 may be used for training a machine learning model or artificial intelligence engine, and may also be combined with historical data or user interaction data in order to create user characteristic data. The learned data storage 324 may include adversarial or extrapolated scenarios or data generated by the systems described herein which may be fed back into artificial intelligence and neural network learning engines 316 to train the authentication system 130. In some embodiments, the authentication system 130 may include an adversarial function configured for providing adversarial learning and modeling to the system by introducing unreliable or erroneous data to the system; a learning or adaptation function for defining system response to data changes or an adaptation rate for implementing changes (i.e., model reconfiguration) within an architecture of the systems described herein; and an alertness function and robustness function for defining an appropriate system reaction, response, or extent of system reaction based on one or more environmental conditions or previous interactions. In some embodiments, various synthetic data may be injected in an outgoing data stream in real-time and over multiple iterations in order to further aid in identifying environmental patterns by analyzing the various responses received in correspondence to the synthetic data.

The artificial intelligence and neural network engines 316 described herein may include engines and/or models directed to, for example, cybersecurity, misappropriation detection, medicine, autonomous deices (e.g., self-driving cars), AI assistants, or the like.

The imaging database 326 is configured for storing received or generated image data used by the authentication system 130. The artificial intelligence and neural network engines 316 described herein generate enriched image data that can then be analyzed by the authentication system 130 to determine high-confidence matching of user identities and verification for the completion of one or more user activities, such as the disbursement of resources. Such generated image data is stored in the imaging database 326. In one embodiment, the imaging database 326 is configured to store a collection of image data collected by the entity system 120 or third party systems 140 in order to provide the authentication system 130 with a large amount of image data that allows the authentication system 130 a high level of adaptability to constantly changing environments or a wide array of various environmental conditions and user characteristics, as may be reflected in changes in a received data stream in real time during implementation of the authentication system 130.

In one embodiment of the invention, the authentication system 130 may associate with applications having computer-executable program code that instructs the processing device 304 to perform certain functions described herein. In one embodiment, the computer-executable program code of an application associated with the user device 110 and/or the entity system 120 may also instruct the processing device 304 to perform certain logic, data processing, and data storing functions of the application. In one embodiment, the authentication system 130 further comprises a dynamic optimization algorithm to be executed by the processing device 304 or a controller 301 for reconfiguring a neural network learning model based on, for example, analyzed performance metrics. That said, the algorithm may further include a data pattern of a streamed data source, a data output from one or more models, or the like during an assessment of a new model reconfiguration. In some embodiments, a dynamic optimization algorithm may further receive the data stream and identified changes to the data stream in real-time for determining any reconfigurations.

In non-limiting embodiments, the data stream includes such as system hardware information (e.g., hardware energy usage) or other non-financial authentication information data (e.g., cybersecurity). In still other embodiments, the data stream may contain data collected by a security system for detecting intrusion (e.g., video monitoring, motion detecting, or the like). In other non-limiting examples of data monitored within the data stream include information regarding past, current, or scheduled transactions or other financial data associated with the user. Transaction information may include transaction amounts, payor and/or payee information, transaction dates and times, transaction locations, transaction frequencies, and the like. In some embodiments, data may include information regarding account usage. For example, the data stream may include information regarding usage of a credit or debit card account such as locations or time periods where the card was used. In another example, the data may further include merchants with whom the user frequently interacts.

In some embodiments, the data stream may contain information regarding characteristics of the data itself which may be monitored by the system. For example, the data stream may contain information regarding the quality of the data (e.g., file size, bit rate of stream), the fidelity of the data (i.e., data accuracy), mutability of the data stream (i.e., how quickly a data pattern in the data stream changes).

The system receives the streaming data where the data is then analyzed and processed by one or more artificial intelligence and neural network engines or models for decisioning purposes. Models, individually and/or structured as clusters, may be trained based on predetermined training data and/or new data acquired in real-time (i.e., from the data stream), wherein the system learns from the data by dynamically identifying patterns as the information is received and processed. In some embodiments of the present invention, models may be adaptive, wherein the models may be reconfigured based on different environmental conditions and/or an analysis and evaluation of the individual model performance. The model may be modified by the system by having one or more individual models and/or clusters added, removed, made inactive, or the like. In another example, the system may weight particular the conclusions of particular models and/or model clusters more than others based on rated accuracy of verification ability. Population architecture refers to a collection and particular arrangement of active models and/or clusters of models that are configured to process information mathematically or computationally to make decisions. Particular models and/or clusters may be weighted by the system to emphasize the impact or contribution of the particular models and/or clusters over others.

Embodiments of the authentication system 130 may include multiple systems, servers, computers or the like maintained by one or many entities. In some embodiments, the authentication system 130 may be part of the entity system 120. In other embodiments, the entity system 120 is distinct from the authentication system 130. The authentication system 130 may communicate with the entity system 120 via a secure connection generated for secure encrypted communications between the two systems either over the network 101 or alternative to the network 101.

FIG. 4 provides an example of thermal measurement and analysis overlay, in accordance with one embodiment of the invention. Shown in diagram (A) of FIG. 4 is one embodiment of a thermally enhanced image that combines the visible spectrum of facial recognition with infrared extension. An original image received by the authentication system 130 may be provided by a number of sources, including a user device 110, entity system 120, third party system 140, an auxiliary device used by the user or placed at an entity or third party location, or captured and provided by the authentication system itself. In some embodiments, the original image may be captured as part of a biometric authentication process, such as a facial recognition process, and may include an image with one or more layers indicating two-dimensional characteristics of the image perspective, three dimensional characteristics of object contours, and the like. The original image is then overlaid with thermal image data captured and mapped as a layer to the original image. As shown in diagram (A), the thermal image data includes a relative measurement of temperature data as the temperature varies across the object surface. For instance, in the embodiment shown in diagram (A), the object shown in the image is a human face with overlaid thermal image data showing relatively colder or warmers areas of the object. In the embodiment of FIG. 4, a colder area is indicated by number 412, a warmer area is indicated by number 410, and an area of measured temperature between these two values is indicated by number 414. This is also indicated by the associated scale shown on the right of the thermally enhanced image at number 416.

Also shown in FIG. 4 is diagram (B), which depicts a location and shape of isothermal curves (labeled as number 420) as learned over time by a trained neural network. The neural network is trained with enhanced thermal spectrum images which combine and utilize both visible spectrum image data and infrared spectrum image data, as described with respect to diagram (A) above. The location of the isothermal curvatures on the object depicted in the thermally enriched image are learned over time with respect to the change in environmental factors, device characteristics associated with the capture of the original image data and thermal image data (e.g. calibration and sensitivity of the device, and the like), and the channel through which the data is collected and received by the authentication system 130. These various time-dependent characteristics are normalized to produce consistency among thermally enriched images and the resulting isometric curvatures. For instance, environmental factors such as ambient temperature, time of day, reflectivity of surrounding surfaces and the like may all affect the infrared spectrum readings that are overlaid on the original image, and thus may affect the isothermal curvature mapped by the trained neural network. For this reason, in some embodiments, the received data may be normalized to remove environmental variances and achieve a precise thermal mapping regardless of environmental, device, and channel variances between data streams over time.

Also shown in FIG. 4 is diagram (C) which depicts thermal gradient readings as shown on the thermally enriched, normalized isothermal curvature diagram (B). The thermal gradient readings reflect dynamic changes and the speed of the location and shape of isothermal curves with respect to changes in the environmental factors (e.g. ambient temperature, which may be controlled by the authentication system 130). These readings and measurements may again be normalized by the trained neural network over time to produce precise results for the generated thermal gradient readings. In some embodiments, the authentication system 130 or entity system 120 may specifically alter ambient temperature or other environmental characteristics related to the object's surroundings in order to predictably produce a varied data set for one or more objects, which can then be extrapolated and used to normalize subsequently received data based on the expected perceived changes in thermal gradient readings. For instance, as depicted in the embodiment of diagram (A), it is clear that the lower temperature areas 412 are consistent with certain features of the object, which in this case coincide with the object's nose and eyebrows. The system may determine, by intentionally altering the environmental conditions during a data dream of the same object, that the rate at which certain other areas of the object's face may cool at a certain, predictable rate, changing the isothermal curvature which coincides with a unique signature of the object characteristics. In this way, the resulting thermally enriched image data is not only analyzed in a static manner, but may be measured and analyzed over time to identify the unique signature associated with a particular object with regard to how the object reacts to various or changing environmental conditions.

Not only does this approach provide an increased amount of data for which to base a unique signature on, but in some embodiments the time dependent variances in thermally enriched images of the object may indicate the liveliness of the object. For instance, as shown in FIG. 4, the object is a human face that would be excepted to have localized areas that are relatively cooler or warmer than others, and such areas may change temperature at a predictable rate and in a predictable order as environmental conditions change. In contrast, a non-living object that contains the same 3D contours as the object shown in FIG. 4, such as a silicone copy, might be designed such that the change of the temperature across the curvature and features of the object change more or less uniformly, indicating that the copy is non-living. This "liveliness" detection may also be achieved by analyzing the movement, gait, and other time dependent features of the object. In still further embodiments, the liveliness detected may be based on the distribution of isothermal lines in a static thermally enriched image. For instance, comparing an inanimate model (e.g., a model created to emulate the surface and contours of a living object, such as a silicone model, 3D printed model, and the like), with an even distribution of temperature readings across the surface as compared to the living object which would show some variance across the surface in temperature readings.

FIG. 5 provides a high level process flow for processing, analysis, and authentication, in accordance with one embodiment of the invention. As shown in FIG. 5 at block 502, the process begins wherein the authentication system 130 receives thermal image data from a thermal sensor or from one or more multi-channel input sources such as a user device, auxiliary device, camera, infrared sensor, and the like. As discussed, such multiple-channel input sources may comprise a number of different entities, locations, and device types which provide an image of a detected object or a thermal image of a detected object that depicts the IR spectrum of the object and surrounding environment. Next, as shown in decision diamond 520, the authentication system 130 performs the liveliness detection step to determine if the object depicted in the received image data is a living object, as opposed to an inanimate model of an object. As discussed with regard to FIG. 4, the inanimate model (e.g., a model created to emulate the surface and contours of a living object, such as a silicone model, 3D printed model, and the like), would be detectable by its even distribution of temperature readings across the surface as compared to the living object which would show some variance across the surface in temperature readings. If the liveliness detection step fails to verify that the object is a living object, the process stops and returns to block 502, wherein more data may be collected for verification, or the authentication system 130 may return a message to one or more systems that the identity of the object cannot be verified. In some embodiments, the system may detect based on conventional biometric indicators, such as 3D contouring or 2D analysis of an object, that the inanimate object may be emulating a known user. In such cases, the authentication system 130 may alert the entity system 120 at which the user maintains an account, or may directly notify the user 102 via the application of the user device 110.

In embodiments where the liveliness detection 520 decision is verified, the authentication system 130 may pass the image data to the neural network engine where it is normalized based on environmental and channel characteristics, as shown in block 504. Based on previously recorded data used to train the neural network engine, the authentication system 130 may identify the location, device type, time of day, season, ambient temperature, and other case-specific characteristics that the authentication system 130 may use to normalize the thermal image data in order to combine the received thermal image data with multi-modal biometric data, as shown in block 506. The normalized, combined thermal image is then enriched to include isothermal curves and normalized thermal gradient coloring via the trained neural network engine, as shown in block 508. Next, the authentication system 130 checks the identification and authentication determination from the neural network and an authentication step is performed to determine if the identity of the object in the enriched image matches a known user identity stored by the authentication system 130, as shown in block 510. As shown in decision diamond 522, this may result in either an approval or denial of the verification of the user identity, which the authentication system 130 may use to deny the user action, resource action, or forward to entity systems 120, third party systems 140, or user 102. Finally, as shown in block 512, if the verification results in a denial, the authentication system 130 may request further authentication information, additional interaction information, or escalate the authentication requirement for the particular instance or for any set number or duration of future interactions with the purported user 102. For instance, the authentication system 130 may require the user 102 to provide a passcode, complete a three step verification process, or may defer to other systems, such as entity system 120 or on site administrators to verify the identity of the user 102 in-person at a brick and mortar location.

FIG. 6 provides a high level process flow for neural network training on multi-modal thermally enriched image data, in accordance with one embodiment of the invention. As in FIG. 5, the embodiment depicted in FIG. 6 begins with acquiring image data from the user device 110, an auxiliary device, or other source such as an entity branch location camera or third party source, as shown in block 602. The liveliness detection decision step 520 acts as a filter in this instance to ensure that only animate objects are being used to train the neural network engine, as shown at 620. This ensures that the neural network engine is only trained to authenticate living objects, as opposed to emulated models of such objects.

Next, the process proceeds to block 604, where the image data is normalized and pre-processed for channel, device, and environment specific characteristics. During the training phase, the authentication system 130 may identify new devices, environments, and ambient conditions, and it is expected that the normalization step 604 may not adequately normalize the data on the first pass given a relatively low amount of known data that may exist in the authentication system 130 data storage regarding the specific characteristics to be normalized. However, as the authentication system 130 repeats iterations of training the neural network engine using a large data set of received image data from varying data sources, devices, and environments, the normalization of received image data is improved to result in a high-confidence normalization process.

As shown in block 606, the process then proceeds to perform thermal processing on the image data for thermal gradients, and isothermal curves to result in a thermally enriched image that includes contours and time-dependent gradients for the object in the image that is being analyzed. The neural network engine is then iteratively trained using thermally enriched images from a multimodal data set that may in include a wide range of devices and environments, resulting in the trained neural network engine, as shown in block 608. The trained neural network engine may be tested and compared to other engines trained using various other data sets in order to compare the accuracy of the engine with respect to one or more other neural network engines and determine a confidence score.

In certain embodiments, the authentication system 130 may proceed to step 610, wherein the system performs an optional step of requesting or acquiring interaction data. Instances that might require the optional step 610 might include instances where a clustered analysis of one or more neural network engines shows a deficiency with identifying a certain subset of data with a high degree of confidence, indicating that the system may need additional data from a certain device, environment, or channel. In other embodiments, a single neural network engine may be deficient as compared to one or more other neural network engines in a certain aspect of identity verification, and the authentication system 130 may review and analyze the data used to train the single neural network engine, and request additional interaction information associated with certain training data that was uniquely included in the training set for the deficient neural network engine. By analyzing the additional interaction data, the authentication system 130 may determine that certain data is unreliable, or may determine additional characteristics of the environment, device, or channel that can be used to further normalize the unreliable data.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, micro-code, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein. As used herein, a processor may be "configured to" perform a certain function in a variety of ways, including, for example, by having one or more special-purpose circuits perform the functions by executing one or more computer-executable program code portions embodied in a computer-readable medium, and/or having one or more application-specific circuits perform the function. As such, once the software and/or hardware of the claimed invention is implemented the computer device and application-specific circuits associated therewith are deemed specialized computer devices capable of improving technology associated with collaborative machine learning and population reconfiguration.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F #.

It will further be understood that some embodiments of the present invention are described herein with reference to flowchart illustrations and/or block diagrams of systems, methods, and/or computer program products. It will be understood that each block included in the flowchart illustrations and/or block diagrams, and combinations of blocks included in the flowchart illustrations and/or block diagrams, may be implemented by one or more computer-executable program code portions. These one or more computer-executable program code portions may be provided to a processor of a special purpose computer for state-based learning and neural network reconfiguration, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system providing the enrichment of biometric data with thermal imaging data for authentication, the system comprising:
    a module containing a memory storage device, a communication device, and a processor, with computer-readable program code stored thereon, wherein executing the computer-readable code is configured to cause the processor to:
        receive image data and thermal data of an object from one or more devices and channels;
        combine the received image data and thermal data to produce thermal image data;
        normalize the thermal image data based on environmental, device, and channel characteristics;
        enrich the thermal image data with multimodal biometric data to produce an enriched biometric thermal image;
        process the enriched biometric thermal image using a trained neural network model, wherein the processing comprises identification of isothermal curves and normalized thermal gradient coloring on the enriched biometric thermal image;
        perform an authentication check on the enriched biometric thermal image using the trained neural network model to determine if the isothermal curves and normalized thermal gradient coloring matches known characteristics for a purported identity of the object; and
        based on the authentication check, verify or deny the purported identity of the object.

2. The system of claim 1, further comprising:
    performing a liveliness detection on the biometric thermal image, wherein the liveliness detection comprises:
        analyzing movement, thermal variation, or and distribution of thermal readings across a surface of the object to determine if the object is inanimate or alive;
        generating an approval if the object is determined to be alive, or generating a denial if the object is determined to be inanimate; and
        proceeding with the remainder of the system steps only if an approval is generated.

3. The system of claim 1, wherein the multimodal biometric data comprises one or more of hand biometric data, face biometric data, facial feature biometric data, or gait biometric data using both visible and infrared images or video.

4. The system of claim 1, wherein the thermal data is received from multiple channels comprising a mobile device, ATM, entity location device, or third party device.

5. The system of claim 1, further comprising intentionally altering the environmental characteristics surrounding the object;
    receiving a variety of thermal images of the object; and
    analyzing the variety of thermal images of the object to produce a dynamic object characteristic pattern.

6. The system of claim 1, wherein the multimodal biometric data further comprises biometric data for multiple features of the object.

7. The system of claim 1, wherein the authentication check fails to determine a match, and the system is further configured to request additional image and thermal data in order to initiate a second attempt at authentication.

8. A computer-implemented method providing the enrichment of biometric data with thermal imaging data for authentication, the computer-implemented method comprising:
    receiving image data and thermal data of an object from one or more devices and channels;
    combining the received image data and thermal data to produce thermal image data;
    normalizing the thermal image data based on environmental, device, and channel characteristics;
    enriching the thermal image data with multimodal biometric data to produce an enriched biometric thermal image;
    processing the enriched biometric thermal image using a trained neural network model, wherein the processing comprises identification of isothermal curves and normalized thermal gradient coloring on the enriched biometric thermal image;
    performing an authentication check on the enriched biometric thermal image using the trained neural network model to determine if the isothermal curves and normalized thermal gradient coloring matches known characteristics for a purported identity of the object; and
    based on the authentication check, verifying or denying the purported identity of the object.

9. The computer-implemented method of claim 8, further comprising:

performing a liveliness detection on the biometric thermal image, wherein the liveliness detection comprises:
analyzing movement, thermal variation, or and distribution of thermal readings across a surface of the object to determine if the object is inanimate or alive;
generating an approval if the object is determined to be alive, or generating a denial if the object is determined to be inanimate; and
proceeding with the remainder of the system steps only if an approval is generated.

10. The computer-implemented method of claim 8, wherein the multimodal biometric data comprises one or more of hand biometric data, face biometric data, facial feature biometric data, or gait biometric data using both visible and infrared images or video.

11. The computer-implemented method of claim 8, wherein the thermal data is received from multiple channels comprising a mobile device, ATM, entity location device, or third party device.

12. The computer-implemented method of claim 8, further comprising intentionally altering the environmental characteristics surrounding the object;
receiving a variety of thermal images of the object; and
analyzing the variety of thermal images of the object to produce a dynamic object characteristic pattern.

13. The computer-implemented method of claim 8, wherein the multimodal biometric data further comprises biometric data for multiple features of the object.

14. The computer-implemented method of claim 8, wherein the authentication check fails to determine a match, and the system is further configured to request additional image and thermal data in order to initiate a second attempt at authentication.

15. A computer program product providing the enrichment of biometric data with thermal imaging data for authentication, the computer program product comprising at least one non-transitory computer-readable medium having computer-readable program code portions embodied therein, the computer-readable program code portions comprising:
an executable portion configured for receiving image data and thermal data of an object from one or more devices and channels;
an executable portion configured for combining the received image data and thermal data to produce thermal image data;
an executable portion configured for normalizing the thermal image data based on environmental, device, and channel characteristics;
an executable portion configured for enriching the thermal image data with multimodal biometric data to produce an enriched biometric thermal image;
an executable portion configured for processing the enriched biometric thermal image using a trained neural network model, wherein the processing comprises identification of isothermal curves and normalized thermal gradient coloring on the enriched biometric thermal image;
an executable portion configured for performing an authentication check on the enriched biometric thermal image using the trained neural network model to determine if the isothermal curves and normalized thermal gradient coloring matches known characteristics for a purported identity of the object; and
an executable portion configured for verifying or denying the purported identity of the object based on the authentication check.

16. The computer program product of claim 15, further comprising:
an executable portion configured for performing a liveliness detection on the biometric thermal image, wherein the liveliness detection comprises:
analyzing movement, thermal variation, or and distribution of thermal readings across a surface of the object to determine if the object is inanimate or alive;
generating an approval if the object is determined to be alive, or generating a denial if the object is determined to be inanimate; and
proceeding with the remainder of the system steps only if an approval is generated.

17. The computer program product of claim 15, wherein the multimodal biometric data comprises one or more of hand biometric data, face biometric data, facial feature biometric data, or gait biometric data using both visible and infrared images or video.

18. The computer program product of claim 15, wherein the thermal data is received from multiple channels comprising a mobile device, ATM, entity location device, or third party device.

19. The computer program product of claim 15, further comprising intentionally altering the environmental characteristics surrounding the object;
receiving a variety of thermal images of the object; and
analyzing the variety of thermal images of the object to produce a dynamic object characteristic pattern.

20. The computer-implemented method of claim 19, wherein the authentication check fails to determine a match, and the system is further configured to request additional image and thermal data in order to initiate a second attempt at authentication.

* * * * *